United States Patent
Trombetta et al.

[11] Patent Number: 5,843,067
[45] Date of Patent: Dec. 1, 1998

[54] ABSORBENT ARTICLE HAVING A CONTAINMENT CUFF

[75] Inventors: Liberatore Antonio Trombetta; Dennis Allen Darby, both of Hamilton, Canada

[73] Assignee: The Procter & Gamble Company, Cincinnati, Ohio

[21] Appl. No.: 743,482

[22] Filed: Nov. 4, 1996

[51] Int. Cl.$^6$ ........................................ A61F 13/15
[52] U.S. Cl. ................ 601/385.2; 601/369; 601/378; 601/355.1; 601/387
[58] Field of Search ............................ 604/369, 378, 604/385.1, 385.2, 387

[56] References Cited

U.S. PATENT DOCUMENTS

| | | |
|---|---|---|
| 3,572,342 | 3/1971 | Lindquist et al. . |
| 4,610,682 | 9/1986 | Kopp . |
| 4,657,539 | 4/1987 | Hasse . |
| 4,695,278 | 9/1987 | Lawson . |
| 4,781,711 | 11/1988 | Houghton et al. ................ 604/378 |
| 5,080,658 | 1/1992 | Igaue et al. ................... 604/385.2 |
| 5,167,653 | 12/1992 | Igaue et al. ................... 604/385.2 |
| 5,267,992 | 12/1993 | Van Tilburg ..................... 604/387 |
| 5,413,570 | 5/1995 | Enloe ............................ 604/385.2 |
| 5,575,785 | 11/1996 | Gryskiewicz et al. . |
| 5,649,917 | 7/1997 | Roberts et al. . |

FOREIGN PATENT DOCUMENTS

| | | |
|---|---|---|
| 0 340 763 | 11/1989 | European Pat. Off. . |
| 0 685 212 A | 12/1995 | European Pat. Off. . |
| WO 95/16422 | 6/1995 | WIPO . |
| WO 96/13996 | 5/1996 | WIPO . |
| WO 96/21680 | 7/1996 | WIPO . |
| WO 96/21681 | 7/1996 | WIPO . |
| WO 96/21682 | 7/1996 | WIPO . |

*Primary Examiner*—Robert A. Clarke
*Assistant Examiner*—K. M. Reichle
*Attorney, Agent, or Firm*—Thomas J. Osborne, Jr.; David M. Weirich; Jacobus C. Rasser

[57] ABSTRACT

The present invention provides an absorbent article including a containment assembly having a topsheet, a backsheet joined to the topsheet and an absorbent core positioned between the topsheet and the backsheet. The absorbent core has longitudinal edges and end edges. A containment cuff extends along each longitudinal edge of the absorbent core. The containment cuff includes a resilient member, an outerwrap covering the resilient member, and a stem portion for securing the containment cuff to the containment assembly. The resilient member has a height and a cross-sectional area. The resilient member is formed from a material that will recover at least about 80% of its original volume after it is compressed about 20% of its original volume. The stem portion has a first edge, a second edge, and a height as measured from its first edge to its second edge. The first edge of the stem portion is secured to the containment assembly inboard of the longitudinal edge of the absorbent core. The containment cuff has a height of the resilient member per height of the stem portion of about 0.04 to about 100 centimeters per centimeter.

19 Claims, 2 Drawing Sheets

ABSORBENT ARTICLE HAVING A CONTAINMENT CUFF

FIELD OF THE INVENTION

The present invention relates to absorbent articles such as incontinence pads, and more particularly, the present invention relates to absorbent articles having containment cuffs which function to prevent leakage of bodily fluids between the absorbent article and the wearer. More particularly, the invention pertains to such absorbent articles having containment cuffs extending along a portion of each longitudinal edge of the absorbent core to prevent leakage of bodily fluids and to improve wearer comfort.

BACKGROUND OF THE INVENTION

There is a growing awareness of the lack of satisfactory products designed for mobile persons with incontinent infirmities. While sanitary napkins, pantiliners, disposable briefs and diapers are available for the mobile incontinent person, such products are not satisfactory from either a comfort or a protection standpoint. Catamenial products, such as pantiliners and sanitary napkins, are very comfortable to use. However, these products fail to achieve a satisfactory level of containment for urine. While diapers and briefs meet the containment needs of the incontinent person, these products lack the comfort and discreteness available from sanitary napkins and pantiliners.

Thus, it is desirable to provide an absorbent article such as an incontinence pad that is comfortable and discrete, yet provides superior protection and containment. In order to achieve the goal of providing such an absorbent article, it is necessary that the absorbent article be capable of accepting and containing fluids discharged from the body; conforming to the body of the wearer; maintaining good body contact (i.e., the maintenance of the absorbent article in close proximity to and in conformity with the body of the wearer); and maintaining its integrity even when wetted so as to be effective to accept and contain a subsequent discharge or gush of liquid.

One prior art method for enhancing the containment of such absorbent articles is to provide the absorbent articles with elasticized leg cuffs. Examples of these type of products are disclosed in U.S. Pat. No. 3,860,003 issued to Buell on Jan. 14, 1975; U.S. Pat. No. 4,909,803 issued to Aziz et al. on Mar. 20, 1990; and U.S. Pat. No. 4,695,278 issued to Lawson on Sep. 22, 1987. Such articles, while providing increased containment for disposable diapers, are often not suitable for use on incontinence pads. This is due to the fact that the elastic member within the cuff often has a small dimension, e.g., a small cross-sectional area, and does not by itself provide the necessary resiliency which conforms to the body of the wearer during usage. Because an absorbent article is subjected to various forces during use, the cuff will tend to loose its shape, and thus its conformity with the wearer's body, resulting in discomfort and the increased likelihood of leakage. For example, traditional cuffs have a tendency to fold inward and block access to the absorbent member or outward causing wearer discomfort and the inability to provide the desired containment.

In order to provide the desired containment, the cuff should have sufficient dimension, e.g., cross-sectional area, to maintain contact with the body during use. If too small, the cuff will not maintain contact with the body potentially leading to leakage of bodily fluids.

Thus, if properly dimensioned and constructed of sufficiently resilient material, the containment cuff can increase the comfort for the wearer while providing improved containment of bodily fluids.

Therefore, it is an object of the present invention to provide an absorbent article which is able to accept and contain bodily fluids without leakage.

It is an additional object of the present invention to provide an absorbent article having improved comfort in both the wet and dry state for the wearer.

These and other objects of the present invention will be more readily apparent when considered and referenced to the following description and when taken in conjunction with accompanying drawings.

SUMMARY OF THE INVENTION

The absorbent article of the present invention includes a containment assembly having a topsheet, a backsheet joined to the topsheet and an absorbent core positioned between the topsheet and the backsheet. The absorbent core has longitudinal edges and end edges. A containment cuff extends along each longitudinal edge of the absorbent core. The containment cuff includes a resilient member, an outerwrap covering the resilient member, and a stem portion for securing the containment cuff to the containment assembly. The resilient member has a height and a cross-sectional area. The resilient member is formed from a material that will recover at least about 80% of its original volume after it is compressed about 20% of its original volume. The stem portion has a first edge, a second edge, and a height as measured from its first edge to its second edge. The first edge of the stem portion is secured to the containment assembly inboard of the longitudinal edge of the absorbent core. The containment cuff has a height of the resilient member per height of the stem portion of about 0.04 to about 100 centimeters per centimeter.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
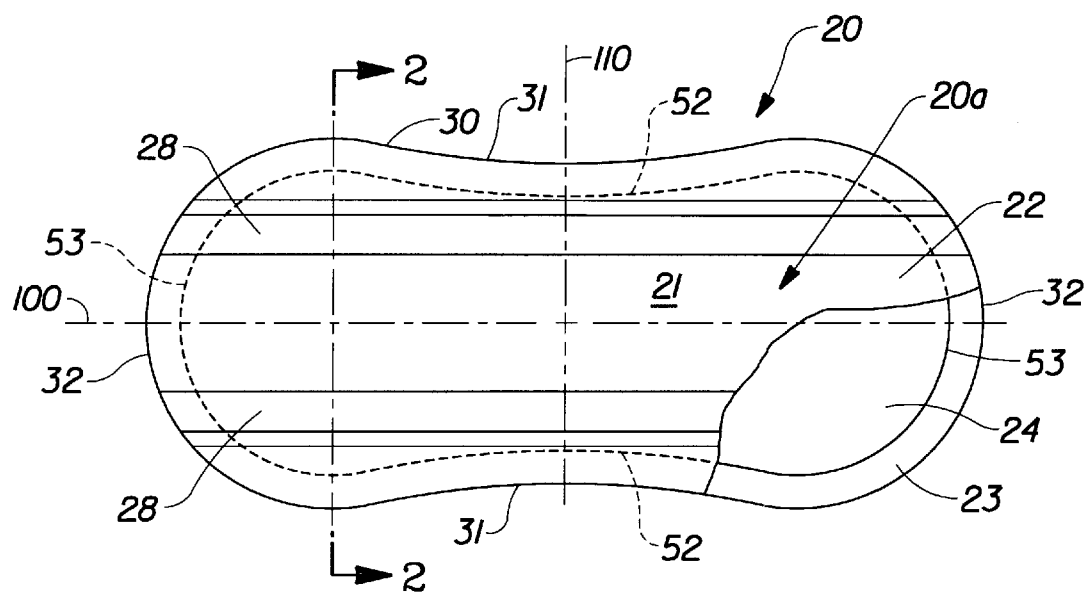
FIG. 1 is a top plan view of an incontinence pad with portions cut-away to more clearly show the construction of the incontinence pad.

A preferred embodiment of a unitary disposable absorbent article of the present invention is the incontinence pad 20 shown in FIG. 1. It should be understood, however, that the present invention is also applicable to other absorbent articles such as sanitary napkins, disposable diapers, incontinence briefs, training pants and the like.

FIG. 1 is a plan view of the incontinence pad 20 of the present invention with portions of the structure being cutaway to more clearly show the construction of the incontinence pad 20 and with the portion of the incontinence pad 20 which faces or contacts the wearer, oriented towards the viewer. As shown in FIG. 1, the incontinence pad 20 preferably comprises a containment assembly 21 comprising a liquid pervious topsheet 22, a liquid impervious backsheet 23 joined with the topsheet 22, and an absorbent core 24 positioned between the topsheet 22 and the backsheet 23. Two containment cuffs 28 are secured to the containment assembly 21. The containment cuffs 28 are disposed one at each side of the incontinence pad 20 in a spaced relation to each other.

The incontinence pad 20 has two surfaces, a body-contacting surface or body facing surface 20a and a garment facing surface 20b. The incontinence pad 20 is shown in FIG. 1 as viewed from its body facing surface 20a. The body facing surface 20a is intended to be worn adjacent to the body of the wearer while the garment facing surface 20b is on the opposite side and is intended to be placed adjacent to the wearer's undergarments when the incontinence pad 20 is worn. The incontinence pad 20 has two centerlines, a longitudinal centerline 100 and a transverse centerline 110. The term "longitudinal" as used herein, refers to a line, axis or direction in the plane of the incontinence pad 20 that is generally aligned with (e.g., approximately parallel to) a vertical plane which bisects a standing wearer into left and right body halves when the incontinence pad 20 is worn. The terms "transverse" or "lateral" as used herein, are interchangeable, and refer to a line, axis or direction which lies within the plane of the incontinence pad 20 that is generally perpendicular to the longitudinal direction. FIG. 1 also shows that the incontinence pad 20 has a periphery 30 which is defined by the outer edges of the incontinence pad 20 in which the longitudinal edges (or "side edges") are designated 31 and the end edges (or "ends") are designated 32.

FIG. 1 shows a preferred embodiment of the incontinence pad 20 in which the topsheet 22 and the backsheet 23 have length and width dimensions generally larger than those of the absorbent core 24. The topsheet 22 and the backsheet 23 extend beyond the edges of the absorbent core 24 to thereby form portions of the periphery 30.

Figure 2:
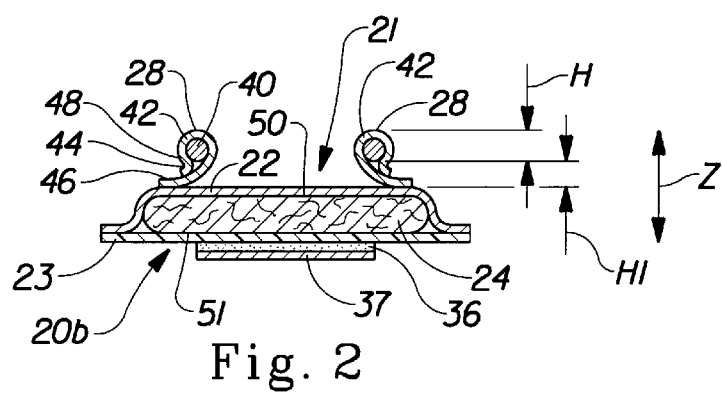
FIG. 2 is a cross-sectional view of the incontinence pad of FIG. 1 taken along section line 2—2.

FIG. 2 is a cross-sectional view of the incontinence pad 20 taken along section line 2—2 of FIG. 1. As can be seen in FIG. 2, the incontinence pad 20 preferably includes an adhesive fastening means 36 for attaching the incontinence pad 20 to the undergarment of the wearer. Removable release liner 37 covers the adhesive fastening means 36 to keep the adhesive from sticking to a surface other than a crotch portion of the undergarment prior to use.

The absorbent core 24 may be any absorbent means which is capable of absorbing or retaining liquids (e.g., menses and/or urine). As shown in FIGS. 1 and 2, the absorbent core 24 has a body facing surface 50, a garment facing surface 51, longitudinal edges 52, and end edges 53. The absorbent core 24 may be manufactured in a wide variety of sizes and shapes (e.g., rectangular, oval, hourglass, dog bone, asymmetric, etc.). The absorbent core 24 is shown in FIGS. 1 and 2 to have an hourglass configuration whereby the longitudinal edges 52 and the end edges 53 are not straight but are curvilinear. The absorbent core 24 may be manufactured from a wide variety of liquid-absorbent materials commonly used in incontinence pads and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the incontinence pad. Further, the size and absorbent capacity of the absorbent core may be varied to accommodate different uses.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; International Publication Number WO 94/28838, published Dec. 22, 1994 in the name of Palumbo, et al.; and International Publication Number WO 94/01069, published Jan. 20, 1994 in the name of Palumbo, et al. Each of these patents are incorporated herein by reference.

The backsheet 23 and topsheet 22 are positioned adjacent the garment facing surface and the body facing surface, respectively, of the absorbent core 24 and are preferably joined thereto and to each other by attachment means (not shown) such as those well known in the art. For example, the backsheet 23 and/or the topsheet 22 may be secured to each other or to other components by a uniform continuous layer of adhesive, a patterned layer of adhesive, or an array of separate lines, spirals, or spots of adhesive; Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 has a body facing surface and a garment facing surface. The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the incontinence pad 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Corporation, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23. An example of a suitable backsheet is disclosed in European Publication No. EPO 0 710 471 published on May 8, 1996 in the name of Depner et al. and in European Publication No. EPO 0 710 472 published on May 8, 1996 in the name of Depner et al.

The topsheet 22 has a body facing surface and a garment facing surface. The topsheet 22 is compliant, soft feeling, and non-irritating to the wearer's skin. Further, the topsheet is liquid pervious permitting liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic film; and thermoplastic scrims. Suitable woven and nonwoven materials can be comprised of natural fibers (e.g., wood or cotton fibers), synthetic fibers (e.g., polymeric fibers such as polyester, polypropylene, polyethylene fibers, or bicomponent fibers) or from a combination of natural and synthetic fibers. A preferred topsheet comprises an apertured formed film. Apertured formed films are preferred for the topsheets because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body facing surface of the formed film topsheet is hydrophilic so as to help liquid to transfer through the topsheet faster than if the body facing surface was not hydrophilic so as to diminish the likelihood that bodily fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body facing surface of the topsheet can be made hydrophilic by treating it with a surfactant such as is described in the above referenced U.S. Pat. No. 4,950,254 issued to Osborn, incorporated herein by reference.

Another suitable topsheet comprises two strips of nonwoven material secured to a formed film. The nonwoven strips are positioned along the longitudinal edges of the incontinence pad. In a preferred embodiment, the nonwoven material is hydrophobic. An example of a topsheet comprising nonwoven material secured to a formed film is described in International Publication Number WO 93/09744, The Procter & Gamble Company, published May 27, 1993 in the name of Sugahara et al. which is incorporated herein by reference.

Another suitable topsheet comprises an upper layer constituted by a nonwoven textile of synthetic fibers, an intermediate layer constituted by a film material, and a lower layer constituted by a nonwoven textile of synthetic fibers. An example of such a topsheet is described in U.S. Pat. No. 4,780,352 issued to Palumbo on Oct. 25, 1988, which is incorporated herein by reference.

The incontinence pad 20 may additionally comprise an acquisition layer positioned between the topsheet 22 and the absorbent core 24. The acquisition layer can be of any desired shape. Suitable shapes include for example, circular, rectangular, triangular, trapezoidal, oblong, dog bone, hourglass, oval, asymmetric, etc. The acquisition layer may have length and width dimensions generally larger or smaller than those of the underlying absorbent core 24. Preferably, the acquisition layer has length and width dimensions less than those of the absorbent core 24.

The acquisition layer may serve several functions including accepting a high rate of fluid intake, serving as a temporary reservoir for the fluid, improving the wicking of fluids over and into the absorbent core, and draining substantially completely into the absorbent core in order to remain empty for subsequent fluid loadings. There are several reasons why the improved wicking of bodily fluids is important, including providing a more even distribution of the bodily fluids throughout the absorbent core. The wicking referred to herein may encompass the transportation of liquids in one, two, or all directions (i.e., in the x-y plane and/or in the z-direction). In addition, this element must resist collapse when wet so that it maintains its performance through multiple loadings. This element must do all these things while also remaining thin.

The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Suitable nonwoven webs include bonded carded webs, spunbonded webs, meltblown webs, and thermally bonded airlaid webs. The acquisition layer may be joined with the topsheet and the absorbent core by any of the conventional means for joining webs together such as adhesives, heat bonds, pressure bonds, ultrasonic bonds, dynamic mechanical bonds, or any other suitable attachment means or combinations of these attachment means as are known in the art.

If the acquisition layer is a nonwoven web, the nonwoven web may be a spunbonded web, a meltblown web, a bonded carded web, or a thermally bonded airlaid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers. In another embodiment, the acquisition layer may be a multilayer material having, for example, at least one layer of a spunbonded web joined to at least one layer of a meltblown web, a bonded carded web, a thermally bonded airlaid web, hydroentangled or other suitable material. Alternatively, the nonwoven web may be a single layer of material such as, for example, a spunbonded web or a meltblown web.

The nonwoven web may also be a composite made up of a mixture of two or more different fibers or a mixture of fibers and particles. Such mixtures may be formed by adding fibers and/or particulates to the gas stream in which the meltblown fibers or spunbonded fibers are carried so that an intimate entangled commingling of fibers and other materials, e.g., wood pulp, staple fibers, superabsorbent materials, and particles occurs prior to collection of the fibers.

In another preferred embodiment, the nonwoven web may be comprised of bicomponent fibers. The bicomponent fiber is preferably a thermobondable bicomponent fiber having an inner core component and an outer sheath component where the inner core component has a higher melting point than the outer sheath component. The ability of the sheath to melt during thermal bonding gives the fiber a heat fusible characteristic. The fiber itself is typically hydrophobic, but can be made hydrophilic by incorporating a surfactant into the sheath of the bicomponent fiber and/or by treating the external surface of the sheath with a surfactant. Exemplary bicomponent fibers and processes for producing the same are described in European Patent Application No. 0 340 763, published Nov. 8, 1989 in the name of Hansen et al. Exemplary acquisition layers having bicomponent fibers are described in U.S. Pat. No. 5,231,122 issued to Palumbo et al. on Jul. 27, 1993; and in International Publication Number WO 94/28838, published Dec. 22, 1994 in the name of Palumbo, et al., each of which is incorporated herein by reference.

The acquisition layer may comprise a composite of bicomponent fibers and other fibers such as rayon, monocomponent synthetic fibers, and tri-component synthetic fibers. For example, the acquisition layer may comprise a blend of 75% bicomponent fibers and 25% rayon fibers.

The acquisition layer should have an operable level of density and basis weight to rapidly acquire and then drain liquid surges into the underlying absorbent core 24, thus remaining relatively empty to receive subsequent liquid surges. The acquisition layer should have sufficient void volume capacity to temporarily retain the amount of liquid that is typically discharged by a wearer during a single insult or surge of liquid into the incontinence pad. Insufficient void volume capacity may result in excessive pooling of liquid against the wearer's skin or excessive run-off of liquid.

The basis weight of the acquisition layer is preferably within the range of from is about 10 to about 300 grams per square meter, more preferably from 20 to about 200 grams per square meter, and most preferably from about 30 to about 60 grams per square meter. The acquisition layer has a thickness of from about 1 to about 10 mm, more preferably from about 1.5 to about 6 mm, still more preferably from about 1.7 to about 4.5 mm, and most preferably from about 2 to about 4 mm, as measured under a pressure of 2 kPa. The acquisition layer has a bulkiness of from about 10 $cm^3/g$ to about 100 $cm^3/g$, more preferably a bulkiness of from about 15 $cm^3/g$ to about 65 $cm^3/g$, still more preferably from about 20 $cm^3/g$ to about 60 $cm^3/g$, and most preferably from about 25 $cm^3/g$ to about 55 $cm^3/g$.

The containment cuffs 28 provide an improved incontinence pad having raised side edges. The containment cuffs 28 are pressed up against the user's skin around the perineal area by the user's undergarment thereby forming a gasketing effect leading to close body contact between the user and the incontinence pad 20. Bodily fluids are thereby directed toward the middle of the incontinence pad 20 through the topsheet and into the underlying absorbent core. In addition, because of the properties of the containment cuffs 28, they retain their shape even when wet, the incontinence pad 20 is capable of handling large insults of bodily fluids without increased likelihood of leakage. Because of its physical properties, the containment cuffs 28 also enhance the comfort perceived by the wearer.

Referring now to FIG. 2, the containment cuffs 28 comprise a resilient member 40, an outerwrap 42 covering the resilient member 40 and a stem portion 44 for securing the containment cuff 28 to the containment assembly 21. Each stem portion 44 has a first edge 46 positioned adjacent to the containment assembly 21 and a second edge 48 spaced from the containment assembly 21 and positioned adjacent the resilient member 40. The stem portion 44 is joined to the containment assembly by an adhesive or other suitable means known in the art. As shown in FIGS. 1 and 2, the stem portion 44 is joined directly to the topsheet 22 of the containment assembly 21 inboard of the longitudinal edge 52 of the absorbent core 24. Accordingly, the containment cuff 28 resides over and above the absorbent core 24. In addition, the first edge 46 of the stem portion 44 is positioned inward of the longitudinal edge 52 of the absorbent core 24. This configuration is preferred as the containment cuff 28 is able to direct fluids downward and into the absorbent core 24 thus preventing leakage of bodily fluids. If spaced outwardly from the longitudinal edges 52 of the underlying absorbent core 24, fluid would not be directed directly into the absorbent core 24 and instead would be allowed to pool along the longitudinal edges of the incontinence pad 20.

In addition to the positioning of the containment cuff 28 on the containment assembly 21, the dimensions of the containment cuff 28, i.e., the dimensions of the resilient member 40 and the stem portion 44, are also critical to the performance of the incontinence pad 20. The resilient member 40 has a height H as measured in a direction parallel to the Z direction or thickness of the absorbent article 20. The resilient member 40 has a cross-sectional area A as measured in a direction generally parallel to the transverse axis 110 of the incontinence pad 20. The height H of the resilient member 40 may be from about 0.2 cm to about 10 cm, more preferably from about 0.5 cm to about 5 cm, and most preferably from about 0.7 cm to about 1 cm. The cross-sectional area A of the resilient member 40 may be from about 0.01 $cm^2$ to about 100 $cm^2$, more preferably from about 0.2 cm² to about 50 cm², and most preferably from about 0.3 cm² to about 1 cm².

The stem portion has a height H1 as measured from the first edge 46 to the second edge 48. The height H1 of the stem portion is dimensioned to be smaller than the height of the resilient member 40. Preferably, the height of the stem portion 44 is less than one-half the height of the resilient member 40. Preferred dimensions for the height of the stem member are from about 0.1 cm to about 5 cm, more preferably from about 0.25 cm to about 2.5 cm, and most preferably from about 0.35 cm to about 0.5 cm. The height H1 of the stem portion which separates the resilient member 40 from the containment assembly 21 provides the containment cuff 28 with the ability to maneuver in correspondence to the movements of the wearer during usage. Without this critical height H1 the resilient member would be secured directly to the absorbent core thus forming a somewhat rigid member, e.g., rigid in the cross or transverse direction of the incontinence pad 20, which may lead to wearer discomfort and an irritation.

While height dimensions of the stem portion and the height dimensions of the resilient member are important, the relationship between the two dimensions is also critical to the performance of the incontinence pad 20. For example, if the height of the stem portion is too large, the containment cuff 28 will simply move and roll over in relation to the position of the body and not provide the desired containment function. If however, the height H1 of the stem portion is too short and the height H of the resilient member 40 is too large, the containment cuff 28 will be bulky and uncomfortable for the wearer. Therefore, the containment cuff 28 preferably has a height H of the resilient member per height H1 of the stem portion of from about 0.04 to about 100 cm/cm, more preferably from about 2 to about 50 cm/cm, and most preferably from about 3 to about 10 cm/cm. This relationship establishes the containment cuffs ability to provide the desired comfort and contact with the body while containing fluids within the incontinence pad 20.

The relationship between the height dimension of the stem portion and the cross-sectional area of the resilient member is also critical to the performance of incontinence pad 20. The containment cuff 28 preferably has a cross-sectional area of the resilient member per height of the stem portion of from about 0.01 to about 785 cm²/cm, more preferably from about 1 to about 100 cm²/cm, and most preferably from about 2 to about 50 cm²/cm. This relationship establishes the containment cuffs ability to provide the desired comfort and contact with the body while containing fluids within the incontinence pad 20.

The relationship between the position of the first edge 46 of the stem portion 44 in relationship to the longitudinal edge 52 of the absorbent core 24 and the height H1 of the stem portion is also critical to the performance of the incontinence pad 20. The first edge 46 is preferably positioned inboard of the longitudinal edge 52 of the absorbent core 24 by a distance greater than the height H1 of the stem portion. This insures that at least a portion of the resilient member and the containment cuff will reside at least over and preferably laterally inwardly of the longitudinal edge 52 of the absorbent core 24. Otherwise, the containment cuff extends beyond the longitudinal edge 52 of the absorbent core 24 causing irritation to the wearer and the loss of immediate contact with the body permitting the potential for leakage of bodily fluids.

In order to provide an incontinence pad 20 which is both comfortable and protective, the resilient members 40 should be compressible, conformable and resilient. That is to say, the resilient members 40 must possess such physical properties so that the force applied to them by the action of the wearer will readily cause them to bend, to compress and to conform to a space available for them as the incontinence pad 20 is held adjacent the wearer's body. The resilient members 40 must be resilient so that each must, without the application of external forces, return essentially to its original size and shape after the forming forces are removed. Preferably, the material used in manufacturing the resilient members 40 possesses such resilience that it will recover at least about 80% of its original volume after it is compressed to about 20% of its original volume when the compressing forces are removed. Most preferably, the material used in manufacturing the resilient members 40 will recover at least about 90% of its original volume after it is compressed to about 50% of its original volume when the compressing forces are removed.

Because the incontinence pad 20 is designed to retain its shape during use, the resilient members 40 must also be essentially unaffected by the presence of liquids such as urine; that is to say, the resilient member 40 must possess a high degree of wet resiliency. The resilient members 40 must retain sufficient inherent resiliency, even when wet, to impart to the containment cuffs sufficient elasticity to resist collapsing during use such that the containment cuffs 28 will retain their shape during use. Certain materials and fibers, such as rayon or cellulose fibers, have a high degree of resiliency in the dry state, but are essentially non-resilient when wetted, such materials and fibers are, in general, not useful in the present invention as resilient members 40. The terms "moisture insensitive" or "liquid insensitive" is used herein to describe materials and fibers whose resiliency is relatively unaffected by the presence of moisture.

The resilient members 40 may be manufactured in a wide variety of sizes and shapes and from a wide variety of materials. As shown in FIG. 2, the resilient members 40 have a substantially circular cross-section and extend substantially along the entire length of the containment assembly 21. The resilient members 40 may extend the entire length of the containment assembly 21 or just along a portion thereof. For example, the resilient members may be positioned only within the central portion of the incontinence pad 20. Alternatively, the resilient members 40 may extend beyond the end edges of the absorbent core 24. Preferably, the resilient members 40 do not extend along the entire length of incontinence pad 20.

The resilient members 40 may also have other cross-sectional configurations other than the circular configuration shown in FIG. 2. For example, the resilient members 40 may be oval, square, rectangular, pentagonal, triangular, elliptical, asymmetric, etc. In addition the resilient members 40 may be formed in a number of ways. The resilient members may be formed by rolling a batt of fibers into a circular configuration. Alternatively, a layer of fibers may be folded or a number of layers may be placed on top of one another to form the resilient members 40. Alternatively, the resilient members 40 may be extruded material into various configurations as desired.

Preferably, the resilient shaping members comprise a synthetic foam material. A suitable synthetic foam material is an extruded, low density, closed-cell polyethylene foam, density range 27–150 kg/m³, or a mixture of closed and opened-cell foams, diameter of about 7 mm. Other synthetic foams useful as the resilient members 40 include polyester foam materials such as those described by DesMarais in U.S. Pat. No. 4,110,276 issued on Aug. 29, 1978 incorporated herein by reference, polyurethane foams, styrene-betadine foams, and cellulose sponge material. The synthetic foams should be soft and flexible, open-celled, and of medium cell size. Its interior surfaces should be hydrophilic. Incorporation of surfactant during foam manufacture or-addition of surfactant to the preformed foam are two suitable methods of ensuring that the interior surfaces are hydrophilic. The foam should have a density of from about 0.1 to about 0.8 grams per cubic centimeter.

Other suitable materials for the resilient members 40 are disclosed in International Publication Numbers WO 96/21680 published on Jul. 18, 1996 in the name of Des-Marais et al., WO 96/21681 published on Jul. 18, 1996 in the name of Stone et al., and WO 96/21682 published on Jul. 18, 1996 in the name of Dyer et al.

Alternatively, the resilient members 40 comprise a mass or batt of moisture insensitive fibers. Synthetic fibers are preferred because they exhibit inherent dry and wet resilience. Other fibers may be used so long as the fibers exhibit dry and wet resilience. For example, fibers that are bonded together at their points of intersection usually exhibit the necessary dry and wet resilience. The resiliency of fibers can be described by the initial modulus of the fibers. Initial modulus can be measured according to A.S.T.M. Standard Method D3822 (Standard Test Method for Textile Properties of Single Textile Fibers) which method is incorporated herein by reference. Fibers are said to be moisture insensitive when their initial modulus in the presence of moisture is at least about 90% of the initial dry state modulus. Synthetic fibers useful in the present invention include those made of cellulose acetate, polyvinyl chloride, polyvinyl idinechloride, acrylic resins, polyvinylacetates, nonsoluble polyvinylalcohols, polyethylenes, polypropylenes, polyamides and preferably, polyesters. Preferred are polyester fibers having a denier of from about 1 to about 15 in length of from about 2 to about 8 cm. As indicated herein, the resiliency of the resilient members 40 can frequently be enhanced if the fibers are bonded together at their points of contact. Thermal bonding can be used or add adhesives such as latex adhesives, can be used to bond the synthetic fibers to one another, the other synthetic fibers include multi-component fibers such as bicomponent or tricomponent fibers. Examples of such fibers are disclosed in European Publication No. EPO 0 340 763 published on Nov. 8, 1989 in the name of Hansen.

As shown in FIG. 2, the outerwrap 42 of a containment cuff 28 completely encases the resilient members 40. While it is unimportant that the outerwrap 42 covering the resilient members 40 completely encase and cover the resilient members 40, it is preferred that at least the outerwrap 42 covers a significant portion of the resilient members 40 such that the outerwrap 42 is the portion of the containment cuff 28 which contacts the wearer's skin. This is preferred, as some materials which are useful as the resilient members 40 may be uncomfortable if placed against the wearer's skin. The outerwrap 42 should be compliant, soft-feeling and non-irritating to the wearer's skin. A suitable outerwrap may be manufactured from a wide range of materials such as woven and nonwoven materials; polymeric materials such as apertured formed thermoplastic films, apertured plastic films, and hydroformed thermoplastic films; reticulated thermoplastic film; and thermoplastic scrims. Suitable woven and nonwoven materials can be comprised of natural fibers (e.g., wood or cotton fibers), synthetic fibers (e.g., polymeric fibers such as polyester, polypropylene, polyethylene fibers or bicomponent fibers) or a combination of natural and synthetic fibers. A preferred outerwrap is a nonwoven material comprised of synthetic fibers.

The outerwrap may be either hydrophilic or hydrophobic depending on the material selected for use as the resilient member. If it is desired that the resilient member have some absorptive capacity, it is preferred that at least a portion of the outerwrap be hydrophilic such that fluid may penetrate the outerwrap and reach the resilient member contained therein.

In use, the incontinence pad 20 can be held in place by any support means or attachment means well-known for such purposes. Preferably, the incontinence pad is placed in the user's undergarment or panty and secured thereto by a fastener such as an adhesive 36. The adhesive 36 provides a means for securing the incontinence pad 20 in the crotch portion of the user's panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the incontinence pad 20 is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The incontinence pad 20 of the present invention is used by removing the release liner 37 and thereafter placing the incontinence pad 20 in a panty so that the adhesive 36 contacts the panty. The adhesive 36 maintains the incontinence pad 20 in its position within the panty during use.

Figure 3:
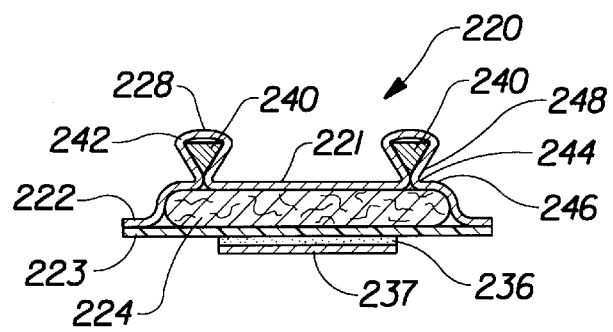
FIG. 3 is a cross-sectional view of another embodiment of an incontinence pad of the present invention.

FIG. 3 is a cross-sectional view of another embodiment of an incontinence pad 220 of the present invention. As shown in FIG. 3, the incontinence pad 220 preferably comprises a containment assembly 221 comprising a liquid pervious topsheet 222, a liquid impervious backsheet 223 joined with the topsheet 222, and an absorbent core 224 positioned between the topsheet 222 and the backsheet 223. The incontinence pad 220 has a pair of containment cuffs 228 positioned on either side of the incontinence pad 220. The incontinence pad 220 preferably includes an adhesive fastening means 236 for attaching the incontinence pad 220 to the undergarment of the wearer. Removable release liner 237 cover the adhesive fastening means 236 to keep the adhesive from sticking to a surface other than a crotch portion of the undergarment prior to use.

As can be seen in FIG. 3, the topsheet 222 forms both the stem portion 244 and the outerwrap 242 of the containment cuffs 228. The outerwrap 242 completely encases the resilient members 240. The resilient members 240 have a substantially triangular cross-section having their apex portion positioned adjacent to the absorbent core 224 and the base portion of the triangular resilient members 240 positioned away from the absorbent core 224.

Figure 4:
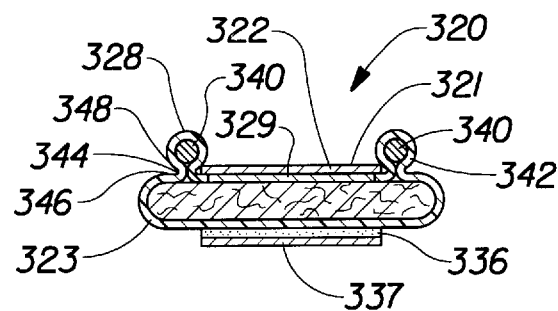
FIG. 4 is a cross-sectional view of another embodiment of an incontinence pad of the present invention.

FIG. 4 is a cross-sectional view of another embodiment of an incontinence pad 320 of the present invention. As shown in FIG. 4, the incontinence pad 320 preferably comprises a containment assembly 321 comprising a liquid pervious topsheet 322, a liquid impervious backsheet 323 joined with the tophseet 322, an absorbent core 324 positioned between the topsheet 322 and the backsheet 323, and an acquisition layer 329 positioned between the topsheet 322 and the absorbent core 324. The incontinence pad 320 has a pair of containment cuffs 328 positioned on either side of the incontinence pad 320. The incontinence pad 320 preferably includes an adhesive fastening means 336 for attaching the incontinence pad 320 to the undergarment of the wearer. Removable release liner 337 covers the adhesive fastening means 336 to keep the adhesive from sticking to the surface other than a crotch portion of the undergarment prior to use.

As can be seen in FIG. 4, the backsheet 323 forms both the stem portion 344 and the outerwrap 342 of the containment cuffs 328. The outerwrap 342 completely encases the resilient members 340. The outerwrap 342 extends inward toward the central portion of the incontinence pad 320 and is secured directly to the topsheet 322.

Figure 5:
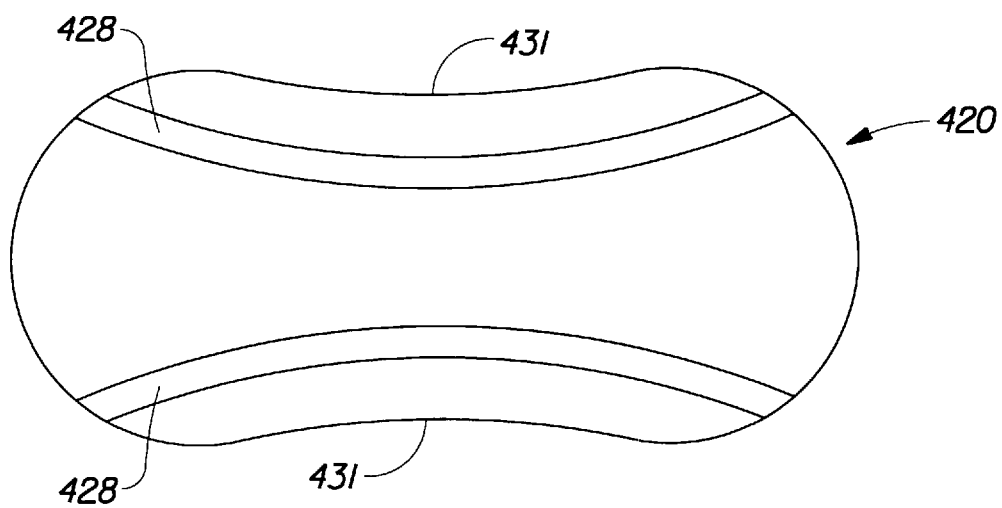
FIG. 5 is a top plan view of another embodiment of an incontinence pad of the present invention.

FIG. 5 is a plan view of another embodiment of an incontinence pad 420 of the present invention. As shown in FIG. 5, the incontinence pad 420 has a pair of containment cuffs 428 positioned along the longitudinal edges of the incontinence pad 420. The containment cuffs 428 have a curvilinear configuration which preferably is parallel to the contour of the longitudinal edge 431 of the incontinence pad 420. Accordingly, the resilient members contained within the containment cuffs 428 also have a curvilinear configuration.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a containment assembly comprising a topsheet, a backsheet joined to said topsheet; and an absorbent core positioned between said topsheet and said backsheet, said absorbent core having longitudinal edges and end edges;
    a containment cuff extending along each longitudinal edge of said absorbent core, said containment cuff comprising a resilient member, an outerwrap completely encasing said resilient member, and a stem portion for securing said containment cuff to said containment assembly, said resilient member having an original volume, a height and a cross-sectional area, said resilient member is formed from a material that will recover at least about 80% of its original volume after it is compressed to about 20% of its original volume, said stem portion having a first edge, a second edge, and a height as measured from its first edge to its second edge, the first edge of said stem portion being secured to said containment assembly inboard of the longitudinal edge of said absorbent core; and
    said containment cuff having a height of said resilient member per height of said stem portion of about 0.04 to about 100 centimeters per centimeter.

2. The absorbent article of claim 1 wherein said outerwrap comprises a portion of said topsheet.

3. The absorbent article of claim 1 wherein said stem portion comprises a portion of said topsheet.

4. The absorbent article of claim 1 wherein said resilient member comprises a liquid insensitive material.

5. The absorbent article of claim 1 wherein said containment cuff has a cross-sectional area of said resilient member per height of said stem portion from about 0.01 to about 785 square centimeters per centimeter.

6. The absorbent article of claim 1 wherein said resilient member has a cross-sectional area from about 0.01 to 100 square centimeters.

7. The absorbent article of claim 1 wherein said resilient member has a height of about 0.2 to about 10 centimeters.

8. The absorbent article of claim 1 wherein said stem portion comprises a portion of said backsheet.

9. The absorbent article of claim 1 wherein said topsheet is liquid pervious.

10. The absorbent article of claim 1 wherein said backsheet is liquid impervious.

11. An absorbent article comprising:
    a containment assembly comprising a liquid pervious topsheet, a liquid impervious backsheet joined to said topsheet; and an absorbent core positioned between said topsheet and said backsheet, said absorbent core having longitudinal edges and end edges;
    a containment cuff extending along each longitudinal edge of said absorbent core, said containment cuff comprising a resilient member, an outerwrap completely encasing said resilient member, and a stem portion for securing said containment cuff to said containment assembly, said resilient member having an original volume, a height and a cross-sectional area, said resilient member is formed from a material that will recover at least about 80% of its original volume after it is compressed to about 20% of its original volume, said stem portion having a first edge, a second edge, and a height as measured from its first edge to its second edge, the first edge of said stem portion being secured to said containment assembly inboard of the longitudinal edge of said absorbent core; and
    said containment cuff having a height of said resilient member per height of said stem portion of about 0.04 to about 100 centimeters per centimeter and a cross-sectional area of said resilient member per height of said stem portion of about 0.01 to about 785 square centimeters per centimeter.

12. The absorbent article of claim 11 wherein said outerwrap comprises a portion of said topsheet.

13. The absorbent article of claim 12 wherein said stem portion comprises a portion of said topsheet.

14. The absorbent article of claim 12 wherein said resilient member comprises a liquid insensitive material.

15. An absorbent article comprising:
    a containment assembly comprising a topsheet having a body-facing surface and a garment-facing surface, a backsheet joined to said topsheet; and an absorbent core positioned between said topsheet and said backsheet, said absorbent core having longitudinal edges and end edges;
    a containment cuff extending along each longitudinal edge of said absorbent core, said containment cuff comprising a resilient member, an outerwrap at least partially covering said resilient member, and a stem portion for securing said containment cuff to said containment assembly, said resilient member having an original volume, a height and a cross-sectional area, said resilient member is formed from a material that will recover at least about 80% of its original volume after it is compressed to about 20% of its original volume, said stem portion having a first edge, a second edge, and a height as measured from its first edge to its second edge, the first edge of said stem portion being secured to the body-facing surface of said topsheet inboard of the longitudinal edge of said absorbent core, and the second edge of said stem portion extending outwardly from said containment assembly; and said containment cuff having a height of said resilient member per height of said stem portion of about 0.04 to about 100 centimeters per centimeter.

16. The absorbent article of claim 15, wherein said stem portion comprises a portion of said backsheet.

17. The absorbent article of claim 15, wherein said resilient member comprises a liquid insensitive material.

18. The absorbent article of claim 15, wherein said containment cuff has a cross-sectional area of said resilient member per height of said stem portion of about 0.01 to about 785 square centimeters per centimeter.

19. The absorbent article of claim 15, wherein said resilient member has a cross-sectional area from about 0.01 to about 100 square centimeters.

* * * * *